United States Patent
Titus et al.

(10) Patent No.: US 9,983,129 B2
(45) Date of Patent: May 29, 2018

(54) EARLY DETECTION OF CELL ACTIVATION BY ATR-FTIR SPECTROSCOPY

(71) Applicant: GEORGIA STATE UNIVERSITY RESEARCH FOUNDATION, INC., Atlanta, GA (US)

(72) Inventors: Jitto Titus, Acworth, GA (US); Chadi Filfili, Suwanee, GA (US); A. G. Unil Perera, Mableton, GA (US); Julia K. Hilliard, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days. days.

(21) Appl. No.: 15/102,091

(22) PCT Filed: Dec. 4, 2014

(86) PCT No.: PCT/US2014/068542
§ 371 (c)(1),
(2) Date: Jun. 6, 2016

(87) PCT Pub. No.: WO2015/085056
PCT Pub. Date: Jun. 11, 2015

(65) Prior Publication Data
US 2016/0305877 A1    Oct. 20, 2016

Related U.S. Application Data

(60) Provisional application No. 61/912,137, filed on Dec. 5, 2013.

(51) Int. Cl.
G01N 21/552    (2014.01)
B07C 5/34      (2006.01)
(Continued)

(52) U.S. Cl.
CPC ......... *G01N 21/552* (2013.01); *B07C 5/3416* (2013.01); *G01N 21/35* (2013.01); *G01N 33/483* (2013.01); *G01N 2021/3595* (2013.01)

(58) Field of Classification Search
CPC ... G01N 21/314; G01N 21/35; G01N 21/3196
See application file for complete search history.

(56) References Cited

U.S. PATENT DOCUMENTS 6,146,897 A * 11/2000 Cohenford ............ G01J 3/28
250/338.1
7,524,681 B2   4/2009 Wolf et al.
(Continued)

OTHER PUBLICATIONS

Cheadle, J. Fan, Y. S. Cho-Chung, T. Werner, J. Ray, L. Do, M. Gorospe and K. G. Becker, BMC genomics 6, 75 (2005).
(Continued)

*Primary Examiner* — Casey Bryant
(74) *Attorney, Agent, or Firm* — Meunier Carlin & Curfman LLC

(57) ABSTRACT

Disclosed are methods, systems, and apparatuses for rapidly detecting a cellular interaction, such as ligand:receptor interactions. For example, the disclosed methods and systems can be used to detect a cellular interaction within 15 minutes to 75 minutes. This allows cells to be used as biosensors to detect cell activating agents in a sample.

17 Claims, 4 Drawing Sheets

(51) Int. Cl.
*G01N 21/35* (2014.01)
*G01N 33/483* (2006.01)

(56) References Cited

U.S. PATENT DOCUMENTS

| | | | |
|---|---|---|---|
| 2004/0121491 A1 | 6/2004 | Marchand-Brynaert | |
| 2010/0130868 A1* | 5/2010 | Hargrove | A61B 5/0075 600/473 |
| 2011/0059023 A1* | 3/2011 | Tunnell | A61B 5/0059 424/9.6 |
| 2012/0225474 A1 | 9/2012 | Wagner | |

OTHER PUBLICATIONS

Crabtree, Science 243 (4889), 355-361 (1989).
Erukhimovitch, E. Bogomolny, M. Huleihil and M. Huleihel, Analyst 136 (13), 2818-2824 (2011).
Erukhimovitch, M. Talyshinsky, Y. Souprun and M. Huleihel, in DNA Viruses (Springer, 2005), pp. 161-172.
Hastings, P. Krug, R. L. Wang, J. Guo, H. P. Lamichhane, T. Tang, Y. S. Hsu, J. Ward, D. Katz and J. Hilliard, Analyst 134 (7), 1462-1471 (2009).
Hilliard, C. Filfili, I. Patrusheva, P. Fuchs, D. Katz, R. Wang, G. Hastings, M. J. Guo, Y.-S. Hsu and J. Ward, NATO, RTO-MP-HFM-182, pp. 29-21.
International Search Report and Written Opinion, issued in International Application No. PCT/US14/68542, dated Apr. 7, 2015.
Lee-Montiel, K. A. Reynolds and M. R. Riley, Journal of biological engineering 5, 16 (2011).
Movasaghi, S. Rehman and I. U. Rehman, Appl Spectrosc Rev 43 (2), 134-179 (2008).
Pinkerneil, et al., "Surface-Attached Polyhistidine-Tag Proteins Characterized by FTIR Difference Spectroscopy", ChemPhysChem 2012, 13, 2649-2653.

* cited by examiner

EARLY DETECTION OF CELL ACTIVATION BY ATR-FTIR SPECTROSCOPY

CROSS-REFERENCE TO RELATED APPLICATIONS

This application claims benefit of U.S. Provisional Application No. 61/912,137, filed Dec. 5, 2013, which is hereby incorporated herein by reference in its entirety.

BACKGROUND

In its simplest form, direct observation of responses, such as cytopathic changes induced by virus infections, has been used historically to screen for viruses in cell culture. Confirmatory assays for specific pathogen identification depend on neutralization assays or complex molecular methods that use biological and chemical probes depending on the signals to be detected. These assays are generally elaborate, and require specific reagents and complex methods usually requiring a range of two hours to weeks where there is sufficient material for detection, or up to months when there is not. Measurement of cellular and/or humoral responses to stimuli is also very useful for the identification of normal immune responses or, alternatively, disease or infection states. Cellular and humoral responses engage immediately after immune defenses detect a foreign agent, a stimulant, an antibody, or a pathogen. Devices and methods are needed that can directly detect these responses as they occur, particularly at the cellular level.

SUMMARY

Disclosed are methods, systems, and devices for rapidly detecting cellular responses to stimuli, such as ligand:receptor interactions. These interactions can take place within seconds-to-minutes, and the disclosed methods can detect these interactions within minutes after they occur. For example, the disclosed methods and systems can be used to detect a cellular interaction within 5 minutes to 120 minutes, such as within 15 minutes to 75 minutes, including within 5, 6, 7, 8, 9, 10, 11, 12, 13, 14, 15, 16, 17, 18, 19, 20, 25, 30, 35, 40, 45, 50, 55, 60, 65, 70, 75, 90, 120, or more minutes. This allows cells to be used as biosensors to detect cell activating agents in a sample.

The disclosed method can involve depositing a sample comprising a homogeneous population of cells under reaction conditions on an internal reflection element (IRE). A beam of infrared (IR) radiation can then be directed through the IRE under conditions such that the IR radiation interacts with the homogeneous population of cells. In preferred embodiments, the IR radiation is an evanescent wave with an average penetration depth of about 2 μm. The average size of the cell ranges from 10-40 μm. An absorption spectrum can then be recorded over a range of preselected frequencies at different times post exposure the cell population. This absorption spectrum can then be compared to a control spectrum from untreated cells to identify differences. In some embodiments, a change in absorbance at one or more frequencies compared to the control spectrum is an indication of a cellular interaction in the homogeneous population of cells. In some embodiments, the reaction conditions comprise exposing the homogeneous population of cells with a sample comprising one or more potential cell activating agents. Examples of potential cell activating agents include pathogens (e.g., virus, bacteria, or yeast) or allergens. Examples of potential cell activating agents also include ligands, such as antibodies, growth factors, cytokines, chemokines, hormones, extracellular matrix proteins, or cell-surface proteins. In addition, the potential cell activating agent can be a protein, peptide, peptide nucleic acid, toxin, or small molecule, e.g., from a combinatorial library. In some embodiments, the reaction conditions comprise contacting the homogeneous population of cells with a sample comprising a change in temperature, pH, salinity, or any combination thereof, compared to the control conditions. The disclosed methods can be used for direct assay of tissues, blood, or other bodily fluids from patient to detect infection within minutes. Other commercial uses can stem from the ability to detect toxins or unidentified biological agents in environmental samples, as is common in biological attacks. The methods can also be used for diagnosis through the detection of disease-causing agents in patient samples, when spectra are compared to those obtained from untreated cells.

Also disclosed is a method for using cells as a biosensor, comprising contacting a plurality of cells with a sample, disposing the plurality of cells on an IRE, directing a beam of IR radiation through the IRE under conditions such that the IR radiation interacts with the homogeneous population of cells, recording an absorption spectrum over a range of preselected frequencies at time points following cell exposures, and comparing the absorption spectra to a control spectra. In this method, a change in absorbances at one or more frequencies compared to the control spectra at similar time points is an indication of a cell activating agent in the sample.

Also disclosed is a system for detecting a cell activating agent in a sample that comprises a Fourier transform infrared spectrometer configured with an IRE for ATR, and a homogeneous population of cells selected to react with the cell activating agent.

The cells used in the disclosed methods and systems can be chosen by one of skill in the art based on the cellular interaction/potential cell activating agent of interest. In some embodiments, the cells are unicellular organisms, e.g., bacterial or yeast cells. In some embodiments, the cells are mammalian cells, e.g., human cells of multiple varieties useful to the purpose of identification. In some embodiments, the cells are from a cell line, such as a transformed cell line. In some embodiments, the cells are genetically or morphologically modified in the lab to enhance their ability to detect specific ligands or conditions, such as cells modified to express specific receptors or pathogen pattern recognition molecules.

The range of preselected frequencies for recording absorbance can be selected based on the agent or pathogen-specific cell responses of interest based on the agent or pathogen-specific diversion of cell defenses in time and place. In general, the preselected frequencies will range between 50 $cm^{-1}$ and 3700 $cm^{-1}$, in particular between 800 $cm^{-1}$ and 1500 $cm^{-1}$.

In preferred embodiments, the IRE is an attenuated total reflectance (ATR) crystal comprising an optical material with a higher refractive index than the sample comprising the plurality of cells. For example, the IRE can be a germanium, zinc selenide, silicon, diamond, or KRS-5 crystal.

In preferred embodiments, the methods and systems involve Fourier Transform Infrared Spectroscopy (FTIR). Therefore, the disclosed methods and systems can further comprise Fourier transformation of the absorbance spectrum. In some embodiments, the ATR crystal is used with a diffractive monochromator instead of an FTIR.

The sample in the above methods and systems can be a biological sample, an environmental sample, or any other sample where a potential agent that derives a cellular response might be present. For example, the biological sample can be a bodily fluid from a subject.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
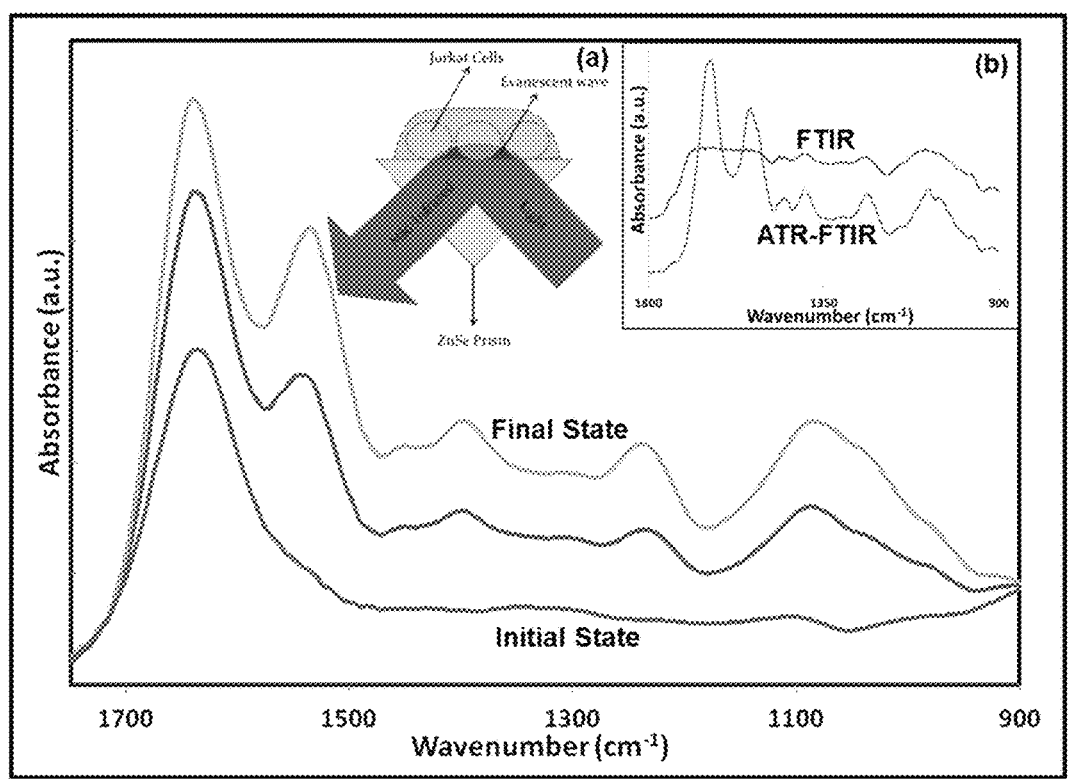
FIG. 1 is an ATR-FTIR spectra of Jurkat cells in medium initially showing the characteristic peaks of the medium and later the peaks representative of the Jurkat cells along with the medium. Inset (a) is a schematic of the ATR technique where a mid-infrared light beam passes through a Zinc Selenide (ZnSe) crystal such that it is totally internally reflected creating an evanescent wave penetrating approximately 2 microns into the cell suspension deposited on the ZnSe crystal which is absorbed by the cell suspension as dictated by the vibrational modes of the components. (The penetration depth and size of the cells are enlarged for clarity). Inset (b) shows the spectra obtained by the conventional transmission mode FTIR and the ATR-FTIR spectroscopy. The ATR-FTIR spectra shows higher signal to noise ratio and better resolved peaks.

The disclosed methods involve the use of an infrared spectrum measuring apparatus. In some embodiments, the apparatus comprises: an internal reflecting element (IRE) comprising a reflection face located on the IRE at a region of intended contact between the IRE and a sample; an infrared radiation source for supplying an evanescent wave of infrared radiation and directing the same from the outside of the IRE to the inside thereof so as to cause the infrared radiation to be incident on the reflection face; and a detector for detecting the once-reflected infrared radiation. Representative, but non-limiting examples of instruments that can provide the infrared radiation source include Fourier Transform Infrared Spectroscopy (FTIR) spectrometers.

The range of preselected frequencies for recording absorbance can be selected based on the cell interactions of interest. In general, the preselected frequencies will range between 50 $cm^{-1}$ and 3700 $cm^{-1}$, in particular between 800 $cm^{-1}$ and 1500 $cm^{-1}$. Table 1 (Applied Spectroscopy Reviews (2008) 43(2):134-179) provides a detailed account of spectral frequencies of the biological tissues.

TABLE 1

The spectral interpretations

| Peak | Assignment |
|---|---|
| 472/5 $cm^{-1}$ | $C_\alpha = C_{\alpha'}$ torsion and C—$OH_3$ torsion of methoxy group |
| 521 $cm^{-1}$ | $C_\alpha = C_{\alpha'}$ torsion and ring torsion of phenyl |
| 600-900 $cm^{-1}$ | CH out-of-plane bending vibrations |
| 606 $cm^{-1}$ | Ring deformation of phenyl |
| 608 $cm^{-1}$ | Ring deformation of phenyl |
| 635 $cm^{-1}$ | OH out-of-plane bend (associated) |
| 700-1000 $cm^{-1}$ | Out-of-plane bending vibrations |
| 793 $cm^{-1}$ | Guanine in a $C_3$'endo/syn conformation in the Z conformation of DNA |
| 802-5 $cm^{-1}$ | Left-handed helix DNA (Z form) |
| 805 $cm^{-1}$ | $C_3$'endo/anti (A-form helix) conformation |
| 813 $cm^{-1}$ | Ring CH deformation |
| 829 $cm^{-1}$ | $C_2$' endo conformation of sugar |
| 831/3 $cm^{-1}$ | $C_2$' endo conformation of sugar |
| 835 $cm^{-1}$ | $C_2$' endo/anti (B-form helix) conformation |
| 835-40 $cm^{-1}$ | Left-handed helix DNA (Z form) |
| 860 $cm^{-1}$ | $C_3$' endo/anti (A-form helix) conformation |
| 868 $cm^{-1}$ | Left-handed helix DNA (Z form) |
| 878 $cm^{-1}$ | $C_3$' endo/anti (A-form helix) conformation |
| 889 $cm^{-1}$ | C—C, C—O deoxyribose |
| 890 $cm^{-1}$ | $C_3$' endo/anti (A-form helix) conformation; $C_2$' endo/anti (B-form helix) conformation |
| 892 $cm^{-1}$ | C—C, C—O deoxyribose Fatty acid, saccharide (β) |
| 900-1300 $cm^{-1}$ | Phosphodiester region |
| 900-1350 $cm^{-1}$ | Phosphodiester stretching bands region (for absorbances due to collagen and glycogen) |
| 925-9 $cm^{-1}$ | Left-handed helix DNA (Z form) |
| 938 $cm^{-1}$ | Unassigned |
| 940 $cm^{-1}$ | Carotenoid |
| 960 $cm^{-1}$ | Symmetric stretching vibration of $v_1 PO_4^{3-}$ (phosphate of HA) |

TABLE 1-continued

The spectral interpretations

Assignment

| | |
|---|---|
| 961 cm$^{-1}$ | C—O deoxyribose, C—C |
| 963 cm$^{-1}$ | δ(C=O) (polysaccharides, pectin) |
| 963/4 cm$^{-1}$ | C—C, C—O deoxyribose |
| 964 cm$^{-1}$ | C—C and C—O in deoxyribose of DNA of tumor cells C—O deoxyribose, C—C |
| 965 cm$^{-1}$ | C—O stretching of the phosphodiester and the ribose |
| 966 cm$^{-1}$ | C—O deoxyribose, C—C DNA |
| 970 cm$^{-1}$ | Symmetric stretching mode of dianionic phosphate monoesters of phosphorylated proteins or cellular nucleic acids DNA |
| 971 cm$^{-1}$ | vPO$_4$ = of nucleic acids and proteins Symmetric stretching mode of dianionic phosphate monoester in phosphorylated proteins, such as phosvitin |
| 972 cm$^{-1}$ | OCH3 (polysaccharides, pectin) |
| 985 cm$^{-1}$ | OCH3 (polysaccharides-cellulose) |
| 994 cm$^{-1}$ | C—O ribose, C—C |
| 995 cm$^{-1}$ | Ring breathing |
| 996 cm$^{-1}$ | C—O ribose, C—C |
| 1000-50 cm$^{-1}$ | Ring stretching vibrations mixed strongly with CH in-plane bending |
| 1000-140 cm$^{-1}$ | Protein amide I absorption |
| 1000-150 cm$^{-1}$ | A reasonably specific area for nucleic acids in the absence of glycogen |
| 1000-200 cm$^{-1}$ | C—OH bonds in oligosaccharides such as mannose & galactose; Mainly from phosphate or oligosaccharide groups; C—O stretching (carbohydrates) |
| 1000-300 cm$^{-1}$ vibrations | CH in-plane bending vibrations - The aromatic CH bending and rocking |
| 1000-350 cm$^{-1}$ | Region of the phosphate vibration - Carbohydrate residues attached to collagen and amide III vibration (in collagen) |
| 1000-650 cm$^{-1}$ | Porphyrin ring of heme proteins |
| 1008 cm$^{-1}$ | CH$_{\alpha, \alpha'}$ out-of-plane bending and C$_{\alpha - C\alpha'}$ torsion |
| 1009/10/1 cm$^{-1}$ | Stretching C—O deoxyribose |
| 1011 cm$^{-1}$ | CH$_{\alpha, \alpha'}$ out-of-plane bending and C$_{\alpha - C\alpha'}$ torsion |
| 1018 cm$^{-1}$ | v(CO), v(CC), δ(OCH), ring (polysaccharides, pectin) |
| 1020 cm$^{-1}$ | DNA |
| 1020-50 cm$^{-1}$ | Glycogen |
| 1022 cm$^{-1}$ | Glycogen |
| 1024 cm$^{-1}$ | Glycogen (C—O stretch associated with glycogen) |
| 1025 cm$^{-1}$ | Carbohydrates peak for solutions Vibrational frequency of —CH2OH groups of carbohydrates (including glucose, fructose, glycogen, etc.); Glycogen; —CH2OH groups and the C—O stretching vibration coupled with C—O bending of the C—OH groups of carbohydrates (including glucose, fructose, glycogen, etc.) |
| 1028 cm$^{-1}$ | Glycogen absorption due to C—O and C—C stretching and C—O—H deformation motions |
| 1029/30 cm$^{-1}$ | O—CH3 stretching of methoxy groups |
| 1030 cm$^{-1}$ | Glycogen vibration, CH2OH vibration; v$_s$ C—O; Collagen & phosphodiester groups of nucleic acids |
| 1030 cm$^{-1}$ | Stretching C—O ribose |
| 1030 cm$^{-1}$ | Collagen |
| 1031 cm$^{-1}$ | v(CC) skeletal cis conformation, v(CH$_2$OH); v(CO) stretching coupled with C—O: Bending; Collagen; One of the triad peaks of nucleic acids (along with 1060 and 1081) |
| 1032 cm$^{-1}$ | O—CH$_3$ stretching of methoxy groups |
| 1033 cm$^{-1}$ | v(CC) skeletal cis conformation, v(CH$_2$OH), v(CO) stretching coupled with C—O bending |
| 1034 cm$^{-1}$ | Collagen |
| 1035 cm$^{-1}$ | Skeletal trans conformation (CC) of DNA; v(CC) skeletal cis conformation, v(CH2OH), n(CO) stretching coupled with C—O bending; Glycogen ; v(CO), v(CC), v(CCO), (polysaccharidescellulose) |
| 1037 cm$^{-1}$ | v(CC) skeletal cis conformation, v(CH$_2$OH), v(CO) stretching coupled with C—O bending |
| 1039/40 cm$^{-1}$ | Stretching C—O ribose |
| 1040-100 cm$^{-1}$ | Symmetric PO$_2$- stretching in RNA and DNA |
| 1045 cm$^{-1}$ | Glycogen band (due to OH stretching coupled with bending); C—O stretching frequencies coupled with C—O bending frequencies of the C—OH groups of carbohydrates (including glucose, fructose, glycogen, etc.); —CH$_2$OH groups and the C—O stretching vibration coupled with C—O bending of the C—OH groups of carbohydrates (including glucose, fructose, glycogen, etc.) |
| 1045/545 cm$^{-1}$ | Gives an estimate carbohydrate concentrations (lower in malignant cells) |

TABLE 1-continued

The spectral interpretations

Assignment

| | |
|---|---|
| 1050 cm$^{-1}$ | $v_s$ C—O—O—C; C—O stretching coupled with C—O bending of the C—OH of carbohydrates; Glycogen |
| 1050-70 cm$^{-1}$ | C—O—C stretching (nucleic acids and phospholipids) |
| 1050-80 cm$^{-1}$ | Indicates a degree of oxidative damage to DNA |
| 1050-100 cm$^{-1}$ | Phosphate & oligosaccharides; PO$_2$- stretching modes, P—O—C antisymmetric stretching mode of phosphate ester, and C—OH stretching of oligosaccharides |
| 1051 cm$^{-1}$ | C—O—C stretching of DNA and RNA |
| 1052 cm$^{-1}$ | Phosphate I band for two different C—O vibrations of deoxyribose in DNA in A and B forms of helix or ordering structure |
| 1053 cm$^{-1}$ | vC—O & δC—O of carbohydrates; Shoulder of 1121 cm$^{-1}$ band, due to DNA |
| 1055 cm$^{-1}$ | Oligosaccharide C—O bond in hydroxyl group that might interact with some other membrane components; Mainly from phospholipid phosphate and partly from oligosaccharide C—OH bonds; Phosphate ester; PO$_2$- stretching and C—OH stretching of oligosaccharides; Phosphate residues; Membrane-bound oligosaccharide C—OH bond (a part of it may originate from the hydroxyl group of the sugar residue); ν(CO), ν(CC), δ(OCH) (polysaccharides, pectin) |
| 1056/7 cm$^{-1}$ | Stretching C—O deoxyribose |
| 1059 cm$^{-1}$ | 2-Methylmannoside Oligosaccharide C—OH stretching band; Mannose & mannose-6-phosphate |
| 1060 cm$^{-1}$ | Stretching C—O deoxyribose; One of the triad peaks of nucleic acids (along with 1031 and 1081 cm$^{-1}$); ν(CO), ν(CC), δ(OCH) (polysaccharidescellulose) |
| 1064 cm$^{-1}$ | Stretching C—O ribose |
| 1065 cm$^{-1}$ | C—O stretching of the phosphodiester and the ribose; Nucleic acids, in the absence of glycogen |
| 1068 cm$^{-1}$ | Stretching C—O ribose |
| 1070 cm$^{-1}$ | Mannose & mannose-6-phosphate |
| 1070-80 cm$^{-1}$ | Nucleic acid band |
| 1071 cm$^{-1}$ | Phosphate I band for two different C—O vibrations of Deoxyribose in DNA in disordering structure |
| 1075 cm$^{-1}$ | Symmetric phosphate stretching modes or ν(PO$_2$-) sym. (phosphate stretching modes originate from the phosphodiester groups in nucleic acids and suggest an increase in the nucleic acids in the malignant tissues); ν(PO$_2$-) symmetric stretching of phosphodiesters |
| 1076 cm$^{-1}$ | Skeletal cis conformation (CC) of DNA |
| 1076 cm$^{-1}$ | Symmetric phosphate [PO$_2$- (sym)] stretching |
| 1078 cm$^{-1}$ | $v_s$ PO$_2$-; Phosphate I in RNA; Symmetric phosphate; Glycogen absorption due to C—O and C—C stretching and C—O—H deformation motions; DNA in healthy samples, in the absence of glycogen; Indicating the role of phosphates during diseases; C—OH stretching band of oligosaccharide residue |
| 1079 cm$^{-1}$ | vs PO$_2$- |
| 1080 cm$^{-1}$ | ν PO$_2$-; Phosphate vibration; Symmetric phosphate [PO$_2$- (sym)] stretching; Collagen & phosphodiester groups of nucleic acids |
| 1081 cm$^{-1}$ | Symmetric phosphate stretching modes or n(PO$_2$-) sym. (phosphate stretching modes originate from the phosphodiester groups in nucleic acids and suggest an increase in the nucleic acids in the malignant tissues); n(PO$_2$-) symmetric stretching of phosphodiesters; Phosphate I in RNA; One of the triad peaks of nucleic acids (along with 1031 and 1060) |
| 1082 cm$^{-1}$ | PO$_2$- symmetric; Phosphate band; Collagen; Symmetric phosphate stretching band of the normal cells |
| 1083 cm$^{-1}$ | PO$_2$- symmetric |
| 1084 cm$^{-1}$ | DNA (band due to PO$_2$- vibrations); Symmetric phosphate [PO$_2$- (sym)] stretching; PO$_2$- symmetric; Stretching PO$_2$- symmetric; Absorbance by the phosphodiester bonds of the phosphate/sugar backbone of nucleic acids; Nucleic acid region; Nucleic acid-phosphate band |
| 1084-6 cm$^{-1}$ | $v_s$(PO$_2$-) of nucleic acids |
| 1085 cm$^{-1}$ | PO$_2$- symmetric (phosphate II); PO$_2$- symmetric; Mainly from absorption bands of the phosphodiester group of nucleic acids and membrane phospholipids, and partially protein (amide III). The band originating from sugar chains (C—OH band) overlaps. Mainly from phospholipid phosphate and partly from oligosaccharide C—OH bonds; Phosphate ester |
| 1086 cm$^{-1}$ | Symmetric phosphate stretching modes or ν(PO$_2$-) sym. (phosphate stretching modes originate from the phosphodiester groups in nucleic acids and suggest an increase in the nucleic acids in the malignant tissues); PO$_2$- symmetric: ν(PO$_2$-) symmetric stretching of phosphodiesters |

TABLE 1-continued

The spectral interpretations

Assignment

| | |
|---|---|
| 1087 cm$^{-1}$ | PO$_2$- symmetric (phosphate II); Symmetric stretching of phosphate groups of phosphodiester linkages in DNA and RNA; Symmetric PO$_2$- stretching in RNA and DNA; Symmetric stretching of phosphate groups in phospholipids |
| 1088-90 cm$^{-1}$ | Phosphate I (stretching PO$_2$- symmetric vibration) in B-form DNA |
| 1089 cm$^{-1}$ | Stretching PO$_2$- symmetric in RNA |
| 1090 cm$^{-1}$ | Mannose & mannose6-phosphate Phosphate ester (C—O—P) band |
| 1090-100 cm$^{-1}$ | Phosphate II (stretching PO$_2$- asymmetric vibration) in A-form RNA |
| 1094 cm$^{-1}$ | Stretching PO$_2$- symmetric (phosphate II); nasym(C—O—C) (polysaccharides-cellulose) |
| 1095 cm$^{-1}$ | Stretching PO$_2$- symmetric |
| 1099/100 cm$^{-1}$ | Stretching PO$_2$- symmetric (phosphate II) |
| 1104 cm$^{-1}$ | Symmetric stretching P—O—C |
| 1105 cm$^{-1}$ | Carbohydrates |
| 1107 cm$^{-1}$ | ν(CO), ν(CC), ring (polysaccharides, pectin) |
| 1110 cm$^{-1}$ | ν(CO), ν(CC) ring (polysaccharides, cellulose) |
| 1113/5 cm$^{-1}$ | Symmetric stretching P—O—C |
| 1117 cm$^{-1}$ | C—O stretching vibration of C—OH group of ribose (RNA) |
| 1119 cm$^{-1}$ | Symmetric stretching P—O—C |
| 1119 cm$^{-1}$ | C—O stretching mode |
| 1120 cm$^{-1}$ | Mannose-6-phosphate Phosphorylated saccharide residue |
| 1121 cm$^{-1}$ | Symmetric phosphodiester stretching band RNA; Shoulder of 1121 cm$^{-1}$ band, due to RNA |
| 1122 cm$^{-1}$ | νC—O of carbohydrates |
| 1125 cm$^{-1}$ | CH$_{2,\,6}$ in-plane bend and C$_1$—C$_\alpha$—H$_\alpha$ bend ν(CO), ν(CC) ring (polysaccharides, cellulose) |
| 1126 cm$^{-1}$ | ν(C—O), disaccharides, sucrose; ν(C—O) + ν(C—C), disaccharides, sucrose |
| 1137 cm$^{-1}$ | Oligosaccharide C—OH stretching band; 2-Methylmannoside |
| 1145 cm$^{-1}$ | Phosphate & oligosaccharides; Oligosaccharide C—O bond in hydroxyl group that might interact with some other membrane components; Membrane-bound oligosaccharide C—OH bond |
| 1150 cm$^{-1}$ | C—O stretching vibration; C—O stretching mode of the carbohydrates; CH$_8$, CH''$_8$ deformations; n(C—O—C), ring (polysaccharides, pectin) |
| 1150-200 cm$^{-1}$ | Phosphodiester stretching bands (sym. and asym.) |
| 1151 cm$^{-1}$ | Glycogen absorption due to C—O and C—C stretching and C—O—H deformation motions |
| 1152 cm$^{-1}$ | CH$_8$, CH$_8$''deformations |
| 1153 cm$^{-1}$ | Stretching vibrations of hydrogen-bonding C—OH groups |
| 1155 cm$^{-1}$ | C—O stretching vibration; ν (C—C)-diagnostic for the presence of a carotenoid structure, most likely a cellular pigment |
| 1159-74 cm$^{-1}$ | νC—O of proteins and carbohydrates |
| 1160 cm$^{-1}$ | CO stretching |
| 1161 cm$^{-1}$ | Stretching vibrations of hydrogen-bonding C—OH groups |
| 1161/2 cm$^{-1}$ | Mainly from the C—O stretching mode of C—OH groups of serine, threosine, & tyrosine of proteins); ν(CC), δ(COH), ν(CO) stretching |
| 1161 cm$^{-1}$ | Stretching modes of the C—OH groups of serine, threonine, and tyrosine residues of cellular proteins; δ(C—O—C), ring (polysaccharides, cellulose) |
| 1163 cm$^{-1}$ | CH'$_9$, CH$_7$, CH'$_7$ deformations |
| 1163/4 cm$^{-1}$ | C—O stretching band of collagen (type I) |
| 1164 cm$^{-1}$ | Mainly from the C—O stretching mode of C—OH groups of serine, threosine, & tyrosine of proteins); ν(CC), δ(COH), ν(CO) stretching; C—O stretching (in normal tissue); Hydrogen-bonded stretching mode of C—OH groups |
| 1170 cm$^{-1}$ | ν$_{as}$ CO—O—C; C—O bands from glycomaterials and proteins |
| 1172 cm$^{-1}$ | Stretching vibrations of nonhydrogen-bonding C—OH groups; CO stretching; CO stretching of collagen (type I); Stretching modes of the C—OH groups of serine, threonine, and tyrosine residues of cellular proteins |
| 1172/3 cm$^{-1}$ | CO stretching of the C—OH groups of serine, threosine, & tyrosine in the cell proteins as well as carbohydrates |
| 1173 cm$^{-1}$ | C—O stretching (in malignant tissues) |
| 1173 cm$^{-1}$ | Non-hydrogen-bonded stretching mode of C—OH groups |
| 1180-300 cm$^{-1}$ | Amide III band region |
| 1185/1/2 cm$^{-1}$ | CH$_2$ |
| 1188 cm$^{-1}$ | Deoxyribose |
| 1200 cm$^{-1}$ | Collagen; Phosphate (P═O) band |
| 1201 cm$^{-1}$ | PO$_2$- asymmetric (phosphate I) |
| 1204 cm$^{-1}$ | Vibrational modes of collagen proteins-amide III; C—O—C, C—O dominated by the ring vibrations of polysaccharides C—O—P, P—O—P; Collagen |

TABLE 1-continued

The spectral interpretations

Assignment

- 1205 cm$^{-1}$ C—O—C, C—O dominated by the ring vibrations of polysaccharides C—O—P, P—O—P
- 1206 cm$^{-1}$ Amide III; Collagen
- 1207 cm$^{-1}$ PO$_2$- asymmetric (phosphate I); Collagen
- 1209 cm$^{-1}$ PO$_2$- asymmetric (phosphate I)
- 1212 cm$^{-1}$ PO$_2$- asymmetric (phosphate I)
- 1217 cm$^{-1}$ PO$_2$- asymmetric (phosphate I)
- 1220 cm$^{-1}$ PO$_2$- asymmetric vibrations of nucleic acids when it is highly hydrogen-bonded Asymmetric hydrogen-bonded phosphate stretching mode
- 1220-4 cm$^{-1}$ Phosphate II (stretching PO$_2$- asymmetric vibration) in B-form DNA
- 1220-40 cm$^{-1}$ Asymmetric PO$_2$- stretching in RNA and DNA
- 1220-50 cm$^{-1}$ vPO$_2$-
- 1220-350 cm$^{-1}$ Amide III (C—N stretching and N—H in plane bending, often with significant contributions from CH$_2$ wagging vibrations)
- 1222 cm$^{-1}$ Phosphate stretching bands from phosphodiester groups of cellular nucleic acids; CH$_{6, 2', \alpha, \alpha'}$ rock
- 1222/3 cm$^{-1}$ PO$_2$- asymmetric (phosphate I)
- 1224 cm$^{-1}$ Collagen; Asymmetric stretching of phosphate groups of phosphodiester linkages in DNA and RNA; Asymmetric PO$_2$- stretching in RNA and DNA; Symmetric stretching of phosphate groups in phospholipids
- 1226 cm$^{-1}$ PO$_2$- asymmetric (phosphate I)
- 1230 cm$^{-1}$ Stretching PO$_2$- asymmetric; Overlapping of the protein amide III and the nucleic acid phosphate vibration
- 1235 cm$^{-1}$ Composed of amide III as well as phosphate vibration of nucleic acids; CH$_{6, 2', \alpha, \alpha'}$ rock
- 1236 cm$^{-1}$ Amide III and asymmetric phosphodiester stretching mode ($v_{as}$PO$_2$-), mainly from the nucleic acids; $v_{as}$PO$_2$- of nucleic acids
- 1236-42 cm$^{-1}$ Relatively specific for collagen and nucleic acids
- 1236/7 cm$^{-1}$ Stretching PO$_2$- asymmetric (phosphate I)
- 1237 cm$^{-1}$ PO$_2$- asymmetric (phosphate I); PO$_2$- asymmetric
- 1238 cm$^{-1}$ Stretching PO$_2$- asymmetric (phosphate I); Asymmetric phosphate [PO$_2$- (asym.)] stretching modes; Stretching PO$_2$- asymmetric; Amide III
- 1238/9 cm$^{-1}$ Asymmetric PO$_2$- stretching
- 1240 cm$^{-1}$ $v_{as}$PO$_2$-; Collagen; Asymmetric non-hydrogen-bonded phosphate stretching mode (phosphate stretching modes originate from the phosphodiester groups of nucleic acids and suggest an increase in the nucleic acids in the malignant tissues); Mainly from absorption bands of the phosphodiester group of nucleic acids and membrane phospholipids, and partially protein (amide III); Amide III; PO$_2$- asymmetric vibrations of nucleic acids when it is non-hydrogen-bonded $v_{as}$PO$_2$-; Collagen; Asymmetric phosphodiester stretching band; Amide III; PO$_2$-ionized asymmetric stretching; v(PO$_2$-) asymmetric stretching of phosphodiesters; Composed of amide III mode of collagen protein and the asymmetric stretching mode of the phosphodiester groups of nucleic acids; Asymmetric stretching mode of phosphodiester groups of nucleic acids; Asymmetric PO$_2$- stretching in RNA
- 1240-45 cm$^{-1}$ Phosphate I (stretching PO$_2$- symmetric vibration) in A-form RNA
- 1240-65 cm$^{-1}$ Amide III (C—N stretching mode of proteins, indicating mainly a-helix conformation)
- 1240-310 cm$^{-1}$ vC—N, amide III
- 1241 cm$^{-1}$ PO$_2$- asymmetric (phosphate I); Phosphate band (phosphate stretching modes originate from the phosphodiester groups of nucleic acids and suggest an increase in the nucleic acids in the malignant tissues; generally, the PO$_2$- groups of phospholipids do not contribute to these bands); Phosphate stretching bands from phosphodiester groups of cellular nucleic acids; $v_{as}$ Phosphate
- 1242 cm$^{-1}$ PO$_2$- asymmetric; Collagen I & IV; Amide III; Amide III collagen
- 1243 cm$^{-1}$ v(PO$_2$-) asymmetric stretching of phosphodiesters; Asymmetric phosphate [PO$_2$- (asym.)] stretching modes (phosphate stretching modes originate from the phosphodiester groups of nucleic acids and suggest an increase the nucleic acids in the malignant tissues) (Generally, the PO$_2$- groups of phospholipids do not contribute to these bands); Phosphate in RNA
- 1243/4 cm$^{-1}$ Collagen (type I)
- 1244 cm$^{-1}$ Collagen I & IV; Asymmetric phosphate stretching ($v_{as}$PO$_2$-)
- 1244/5 cm$^{-1}$ PO$_2$- asymmetric (phosphate I)
- 1245 cm$^{-1}$ PO$_2$- asymmetric
- 1246 cm$^{-1}$ PO$_2$- asymmetric
- 1247 cm$^{-1}$ PO$_2$- asymmetric (phosphate I)
- 1248 cm$^{-1}$ PO$_2$- asymmetric
- 1250 cm$^{-1}$ Amide III TABLE 1-continued The spectral interpretations Assignment 1250-400 cm$^{-1}$ CH$_2$ wagging vibration of the acyl chains (phospholipids)
1255 cm$^{-1}$ Amide III
1256 cm$^{-1}$ PO$_2$- asymmetric (phosphate I)
1262 cm$^{-1}$ PO$_2$- asymmetric (phosphate I)
1265 cm$^{-1}$ PO$_2$- asymmetric (phosphate I); CH$_{\alpha'}$ rocking
1272/3 cm$^{-1}$ CH$_{\alpha'}$ rocking
1276 cm$^{-1}$ N—H thymine
1278 cm$^{-1}$ Vibrational modes of collagen proteins-amide III
1278/9 cm$^{-1}$ Deformation N—H
1280 cm$^{-1}$ Collagen; Amide III
1282 cm$^{-1}$ Amide III band components of proteins; Collagen
1283 cm$^{-1}$ Collagen
1283-1339 cm$^{-1}$ Collagen
1284 cm$^{-1}$ Amide III band components of proteins; Collagen
1287 cm$^{-1}$ Deformation N—H
1288 cm$^{-1}$ N—H thymine
1291/2 cm$^{-1}$ N—H thymine
1294/5/6 cm$^{-1}$ Deformation N—H cytosine
1306 cm$^{-1}$ Unassigned band
1307 cm$^{-1}$ Amide III
1310 cm$^{-1}$ Amide III
1312 cm$^{-1}$ Amide III band components of proteins
1317 cm$^{-1}$ Amide III band components of proteins; Collagen
1327/8 cm$^{-1}$ Stretching C—N thymine, adenine
1328 cm$^{-1}$ Benzene ring mixed with the CH in-plane bending from the phenyl ring and the ethylene bridge
1330 cm$^{-1}$ CH$_2$ wagging
1335 cm$^{-1}$ δ(CH), ring (polysaccharides, pectin)
1335 cm$^{-1}$ δ(CH), ring (polysaccharides, pectin)
1336 cm$^{-1}$ δ(CH), ring (polysaccharides, cellulose)
1337 cm$^{-1}$ Collagen
1337/8 cm$^{-1}$ CH$_2$ wagging
1339 cm$^{-1}$ Collagen; In-plane C—O stretching vibration combined with the ring stretch of phenyl
1340 cm$^{-1}$ CH$_2$ wagging; Collagen
1358 cm$^{-1}$ Stretching C—O, deformation C—H, deformation N—H
1367 cm$^{-1}$ Stretching C—O, deformation C—H, deformation N—H
1368 cm$^{-1}$ δ(CH2), ν(CC) (polysaccharides, pectin)
1369/70 cm$^{-1}$ Stretching C—N cytosine, guanine
1370/1 cm$^{-1}$ Stretching C—O, deformation C—H, deformation N—H
1370/1/3 cm$^{-1}$ Deformation N—H, C—H
1373 cm$^{-1}$ Stretching C—N cytosine, guanine
1380 cm$^{-1}$ δCH$_3$ Stretching C—O, deformation C—H, deformation N—H
1390 cm$^{-1}$ Carbon particle
1395 cm$^{-1}$ Less characteristic, due to aliphatic side groups of the amino acid residues
1396 cm$^{-1}$ Symmetric CH3 bending of the methyl groups of proteins
1398 cm$^{-1}$ CH$_3$ symmetric deformation
1399 cm$^{-1}$ Extremely weak peaks of DNA & RNA-arises mainly from the vibrational modes of methyl and methylene groups of proteins and lipids and amide groups; Symmetric CH3 bending modes of the methyl groups of proteins; δ[(CH$_3$)] sym.; δ[C(CH$_3$)$_2$] symmetric
1400 cm$^{-1}$ Symmetric stretching vibration of COO$_2$ group of fatty acids and amino acids; dsCH3 of proteins; Symmetric bending modes of methyl groups in skeletal proteins; Specific absorption of proteins; Symmetric stretch of methyl groups in proteins
1400-500 cm$^{-1}$ Ring stretching vibrations mixed strongly with CH in-plane bending
1400/1 cm$^{-1}$ COO$_2$ symmetric stretching of acidic amino acids aspartate and glutamate
1400/1/2 cm$^{-1}$ CH$_3$ symmetric deformation
1401 cm$^{-1}$ Symmetric CH$_3$ bending modes of the methy l groups of proteins; δ[(CH3)l sym.; COO$_2$ symmetric stretching of fatty acids
1401/2 cm$^{-1}$ Symmetric CH$_3$ bending modes of the methyl groups of proteins; δ[(CH$_3$)] sym.; Stretching C—N, deformation N—H, deformation C—H; δ[C(CH$_3$)$_2$] symmetric
1403 cm$^{-1}$ Symmetric CH$_3$ bending modes of the methyl groups of proteins; δ[(CH$_3$)] sym.; dsCH3 of collagen; δ[C(CH$_3$)$_2$] symmetric
1404/5 cm$^{-1}$ CH$_3$ asymmetric deformation
1412/4 cm$^{-1}$ Stretching C—N, deformation N—H, deformation C—H
1416 cm$^{-1}$ Deformation C—H, N—H, stretching C—N
1417 cm$^{-1}$ Stretching C—N, deformation N—H, deformation C—H
1418/9 cm$^{-1}$ Deformation C—H
1419 cm$^{-1}$ ν$_s$(COO$^-$) (polysaccharides, pectin)
1430 cm$^{-1}$ δ(CH$_2$) (polysaccharides, cellulose)
1444 cm$^{-1}$ δ(CH$_2$), lipids, fatty acids; δ(CH) (polysaccharides, pectin)

TABLE 1-continued

The spectral interpretations

| | Assignment |
|---|---|
| 1449 cm$^{-1}$ | Asymmetric CH3 bending of the methyl groups of proteins |
| 1450 cm$^{-1}$ | Methylene deformation in biomolecules; Polyethylene methylene deformation modes |
| 1451 cm$^{-1}$ | Asymmetric CH3 bending modes of the methyl groups of proteins; δ[(CH$_3$)] asym. |
| 1454 cm$^{-1}$ | Asymmetric methyl deformation |
| 1455 cm$^{-1}$ | C—O—H; Less characteristic, due to aliphatic side groups of the amino acid residues δ$_{as}$CH$_3$ of proteins; Symmetric bending modes of methyl groups in skeletal proteins |
| 1455/6 cm$^{-1}$ | Asymmetric CH3 bending modes of the methyl groups of proteins; δ[(CH$_3$)] asym. |
| 1456 cm$^{-1}$ | CH$_3$ bending vibration (lipids and proteins) |
| 1457 cm$^{-1}$ | Extremely weak peaks of DNA & RNA-arises mainly from the vibrational modes of methyl and methylene groups of proteins and lipids and amide groups; Asymmetric CH3 bending modes of the methyl groups of proteins; δ[(CH$_3$)] asym. |
| 1458 cm$^{-1}$ | δ$_{as}$CH$_3$ of collagen |
| 1462 cm$^{-1}$ | Paraffin |
| 1465 cm$^{-1}$ | CH$_2$ scissoring mode of the acyl chain of lipid |
| 1467 cm$^{-1}$ | Cholesterol-methyl band |
| 1468 cm$^{-1}$ | δCH$_2$; δCH2 of lipids; CH$_2$ bending vibration (lipids and proteins) |
| 1469 cm$^{-1}$ | CH$_2$ bending of the acyl chains of lipids; CH$_2$ scissoring vibration of the acyl chains (phospholipids) |
| 1470 cm$^{-1}$ | CH$_2$ bending of the methylene chains in lipids |
| 1480 cm$^{-1}$ | Polyethylene methylene deformation modes |
| 1480-543 cm$^{-1}$ | Amide II |
| 1480-600 cm$^{-1}$ | The region of the amide II band in tissue proteins. Amide II mainly stems from the C—N stretching and C—N—H bending vibrations weakly coupled to the C═O stretching mode |
| 1482 cm$^{-1}$ | Benzene |
| 1482/3/5 cm$^{-1}$ | C$_8$—H coupled with a ring vibration of guanine |
| 1486 cm$^{-1}$ | Deformation C—H |
| 1487/8 cm$^{-1}$ | C═C, deformation C—H |
| 1488/9 cm$^{-1}$ | Deformation C—H |
| 1489 cm$^{-1}$ | In-plane CH bending vibration |
| 1490 cm$^{-1}$ | C═C, deformation C—H; In-plane CH bending vibration |
| 1494 cm$^{-1}$ | In-plane CH bending vibration |
| 1495/6 cm$^{-1}$ | C═C, deformation C—H |
| 1500 cm$^{-1}$ | In-plane CH bending vibration from the phenyl rings; CH in-plane bending |
| 1500-60 cm$^{-1}$ | Amide II (an N—H bending vibration coupled to C—N stretching |
| 1504 cm$^{-1}$ | In-plane CH bending vibration from the phenyl rings |
| 1510 cm$^{-1}$ | In-plane CH bending vibration from the phenyl rings; CH in-plane bend |
| 1514 cm$^{-1}$ | ν(C═C)-diagnostic for the presence of a carotenoid structure, most likely a cellular pigment |
| 1517 cm$^{-1}$ | Amide II |
| 1524 cm$^{-1}$ | Stretching C═N, C═C |
| 1526 cm$^{-1}$ | C═N guanine |
| 1527 cm$^{-1}$ | Stretching C═N, C═C |
| 1528 cm$^{-1}$ | C═N guanine |
| 1529/30 cm$^{-1}$ | C═N adenine, cytosine |
| 1530 cm$^{-1}$ | Stretching C═N, C═C |
| 1531 cm$^{-1}$ | Modified guanine? |
| 1532 cm$^{-1}$ | Stretching C═N, C═C |
| 1534 cm$^{-1}$ | Modified guanine; Amide II |
| 1535/7 cm$^{-1}$ | Stretching C═N, C═C |
| 1540 cm$^{-1}$ | Protein amide II absorption- predominantly β-sheet of amide II; Amide II |
| 1540-650 cm$^{-1}$ | Amide II |
| 1541 cm$^{-1}$ | Amide II absorption (primarily an N—H bending coupled to a C—N stretching vibrational mode); Amide II |
| 1543 cm$^{-1}$ | Amide II |
| 1544 cm$^{-1}$ | Amide II bands (arises from C—N stretching & CHN bending vibrations) |
| 1545 cm$^{-1}$ | Protein band; Amide II (dN—H, nC—N); Peptide amide II |
| 1549 cm$^{-1}$ | Amide II; Amide II of proteins |
| 1550 cm$^{-1}$ | Amide II; Amide II of proteins; N—H bending and C—N stretching |
| 1550-650 cm$^{-1}$ | Ring stretching vibrations with little interaction with CH in-plane bending |
| 1550-800 cm$^{-1}$ | Region of the base vibrations |
| 1552 cm$^{-1}$ | Ring base |
| 1553 cm$^{-1}$ | CO stretching; Predominately a-sheet of amide II (Amide II band mainly stems from the C—N stretching and C—N—H bending vibrations weakly coupled to the C═O stretching mode) |

TABLE 1-continued

The spectral interpretations

Assignment

| | | |
|---|---|---|
| 1555 cm$^{-1}$ | Ring base |
| 1559 cm$^{-1}$ | Ring base |
| 1567 cm$^{-1}$ | Ring base |
| 1570 cm$^{-1}$ | Amide II |
| 1571/3 cm$^{-1}$ | C=N adenine |
| 1574/5 cm$^{-1}$ | C=N adenine |
| 1576 cm$^{-1}$ | C=N adenine |
| 1577 cm$^{-1}$ | Ring C—C stretch of phenyl |
| 1581 cm$^{-1}$ | Ring C—C stretch of phenyl |
| 1589 cm$^{-1}$ | Ring C—C stretch of phenyl |
| 1592 cm$^{-1}$ | C=N, NH$_2$ adenine |
| 1594 cm$^{-1}$ | Ring C—C stretch of phenyl |
| 1596 cm$^{-1}$ | Methylated nucleotides |
| 1597 cm$^{-1}$ | C=N, NH$_2$ adenine |
| 1600-720 cm$^{-1}$ | The region of the amide I band of tissue proteins (highly sensitive to the conformational changes in the secondary structure; amide I band is due to in-plane stretching of the C=O bond, weakly coupled to stretching of the C—N and in-plane bending of the N—H bond) |
| 1600-800 cm$^{-1}$ | C=O stretching (lipids) |
| 1601/2 cm$^{-1}$ | C=N cytosine, N—H adenine |
| 1603/4 cm$^{-1}$ | C=N, NH$_2$ adenine |
| 1604 cm$^{-1}$ | Adenine vibration in DNA |
| 1605 cm$^{-1}$ | $v_{as}$(COO$^-$) (polysaccharides, pectin) |
| 1606 cm$^{-1}$ | Adenine vibration in DNA |
| 1609 cm$^{-1}$ | Adenine vibration in DNA |
| 1618 cm$^{-1}$ | Ring C—C stretch of phenyl |
| 1620 cm$^{-1}$ | Peak of nucleic acids due to the base carbonyl stretching and ring breathing mode |
| 1630-700 cm$^{-1}$ | Amide I region |
| 1632 cm$^{-1}$ | Ring C—C stretch of phenyl |
| 1632/4 cm$^{-1}$ | C=C uracyl, C=O |
| 1635 cm$^{-1}$ | β-sheet structure of amide I; Proportion of b-sheet secondary structures (shoulder) |
| 1637 cm$^{-1}$ | C=C uracyl, C=O |
| 1638/9 cm$^{-1}$ | C=C thymine, adenine, N—H guanine |
| 1639 cm$^{-1}$ | Amide I |
| 1640 cm$^{-1}$ | Amide I band of protein and H—O—H deformation of water |
| 1642 cm$^{-1}$ | C$_5$ methylated cytosine |
| 1643 cm$^{-1}$ | Amide I band (arises from C=O stretching vibrations) |
| 1644 cm$^{-1}$ | Amide I |
| 1646 cm$^{-1}$ | Amide I; C$_5$ methylated cytosine; C=O, stretching C=C uracyl, NH$_2$ guanine |
| 1647/8 cm$^{-1}$ | Amide I in normal tissues-for cancer is in lower frequencies |
| 1649 cm$^{-1}$ | Unordered random coils and turns of amide I; C=O, C=N, N—H of adenine, thymine, guanine, cytosine; O—H bending (water) |
| 1650 cm$^{-1}$ | Amide I absorption (predominantly the C=O stretching vibration of the amide C=O); Protein amide I absorption; C=O, stretching C=C uracyl, NH$_2$ guanine; Peptide amide I |
| 1652 cm$^{-1}$ | Amide I |
| 1652/3 cm$^{-1}$ | C$_2$=O cytosine |
| 1653/4 cm$^{-1}$ | C=O, C=N, N—H of adenine, thymine, guanine, cytosine |
| 1655 cm$^{-1}$ | Amide I (of proteins in α-helix conformation); Amide I (ν C=O, δ C—N, δ N—H); C=O cytosine; C55O, C55N, N—H of adenine, thymine, guanine, cytosine; Peak of nucleic acids due to the base carbonyl stretching and ring breathing mode; Amide I has some overlapping with the carbonyl stretching modes of nucleic acid; Amide I (α-helix) |
| 1656 cm$^{-1}$ | Amide I; C$_2$=O cytosine |
| 1657 cm$^{-1}$ | α-helical structure of amide I |
| 1658 cm$^{-1}$ | C=O, stretching C=C uracyl, NH$_2$ guanine; Amide I |
| 1659 cm$^{-1}$ | Amide I |
| 1660 cm$^{-1}$ | Amide I band; ν(C=C) cis, lipids, fatty acids |
| 1664/5 cm$^{-1}$ | C=O Cytosine, uracyl |
| 1665 cm$^{-1}$ | Amide I (disordered structure-solvated) |
| 1666 cm$^{-1}$ | C=O stretching vibration of pyrimidine base |
| 1670 cm$^{-1}$ | Amide I (anti-parallel β-sheet); ν(C=C) trans, lipids, fatty acids |
| 1679 cm$^{-1}$ | Stretching C55O vibrations that are H-bonded (changes in the C=O stretching vibrations could be connected with destruction of old H-bonds and creation of the new ones); C=O guanine deformation N—H in plane |
| 1680 cm$^{-1}$ | Unordered random coils and turns of amide I |
| 1681/4 cm$^{-1}$ | C=O Guanine deformation N—H in plane |
| 1684 cm$^{-1}$ | C=O Guanine deformation N—H in plane |

TABLE 1-continued

The spectral interpretations

| Assignment | |
|---|---|
| 1685 cm$^{-1}$ | Amide I (disordered structure-non-hydrogen bonded) |
| 1690 cm$^{-1}$ | Peak of nucleic acids due to the base carbonyl stretching and ring breathing mode |
| 1694 cm$^{-1}$ | A high frequency vibration of an anti-parallel β-sheet of amide I (the amide I band is due to in-plane stretching of the C=O band weakly coupled to stretching of the C—N and in-plane bending of the N—H bond) |
| 1698/9 cm$^{-1}$ | $C_2$=O guanine; N—H thymine |
| 1700-15 cm$^{-1}$ | The region of the bases |
| 1700-800 cm$^{-1}$ | Fatty acid esters |
| 1700/2 cm$^{-1}$ | C=O guanine |
| 1702 cm$^{-1}$ | C=O thymine; Stretching (C=O) vibrations that are H-bonded (changes in the C=O stretching vibrations could be connected with destruction of old H-bonds and creation of the new ones) |
| 1706/7 cm$^{-1}$ | C=O thymine |
| 1707 cm$^{-1}$ | C=O guanine |
| 1708 cm$^{-1}$ | C=O thymine |
| 1712/9 cm$^{-1}$ | C=O |
| 1713/4/6 cm$^{-1}$ | C=O thymine |
| 1717 cm$^{-1}$ | C=O thymine; Amide I (arises from C=O stretching vibration); C=O stretching vibration of DNA and RNA; C=O stretching vibration of purine base |
| 1719 cm$^{-1}$ | C=O |
| 1725-45 cm$^{-1}$ | C=O stretching band mode of the fatty acid ester |
| 1728/9 cm$^{-1}$ | C=O band |
| 1730 cm$^{-1}$ | Absorption band of fatty acid ester; Fatty acid ester band |
| 1736 cm$^{-1}$ | C=O stretching (lipids) |
| 1739 cm$^{-1}$ | ν(C=O) (polysaccharides, hemicellulose) |
| 1740 cm$^{-1}$ | C=O; C=O stretching (lipids); Ester C=O stretching vibration (phospholipids) |
| 1743 cm$^{-1}$ | C=O stretching mode of lipids |
| 1745 cm$^{-1}$ | Ester group (C=O) vibration of triglycerides; ν(C=O) (polysaccharides, pectin) |
| 1750 cm$^{-1}$ | ν(C=C) lipids, fatty acids |
| 1997/2040/53/58 cm$^{-1}$ | The band of second order |
| 2100 cm$^{-1}$ | A combination of hindered rotation and O—H bending (water) |
| 2600 cm$^{-1}$ | H-bonded NH vibration band |
| 2633/678 cm$^{-1}$ | Stretching N—H ($NH_3^+$) |
| 2727/731 cm$^{-1}$ | Stretching N—H ($NH_3^+$) |
| 2761 cm$^{-1}$ | $CH_3$ modes |
| 2765/66/69/99 cm$^{-1}$ | Stretching N—H ($NH_3^+$) |
| 2800 cm$^{-1}$ | Stretching N—H ($NH_3^+$) |
| 2800-3000 cm$^{-1}$ | C—H: Lipid region; $CH_3$, $CH_2$-lipid and protein |
| 2800-3100 cm$^{-1}$ | C—H stretching vibrations of methyl ($CH_3$) & methylene ($CH_2$) groups & olefins |
| 2800-3500 cm$^{-1}$ | Cholesterol, phospholipids and creatine (higher in normal tissues); Stretching vibrations of CH2 & CH3 of phospholipids, cholesterol and creatine |
| 2802/12/20/21/4/34 cm$^{-1}$ | Stretching N—H ($NH_3^+$) |
| 2834 cm$^{-1}$ | Symmetric stretching of methoxy |
| 2836 cm$^{-1}$ | Stretching N—H ($NH_3^+$) |
| 2838 cm$^{-1}$ | Stretching C—H; Symmetric stretching of methoxy |
| 2846 cm$^{-1}$ | Symmetric stretching of methoxy |
| 2848 cm$^{-1}$ | Cholesterol, phospholipids, and creatine (higher in normal tissues); Stretching vibrations of $CH_2$ & $CH_3$ of phospholipids, cholesterol, and creatine |
| 2849 cm$^{-1}$ | Stretching C—H |
| 2850 cm$^{-1}$ | C—H stretching bands; Stretching C—H; $ν_s$ $CH_2$, lipids, fatty acids; $CH_2$ symmetric |
| 2851 cm$^{-1}$ | Symmetric $CH_2$ stretch |
| 2852 cm$^{-1}$ | $ν_s$ $CH_2$; Symmetric stretching vibration of $CH_2$ of acyl chains (lipids) |
| 2853 cm$^{-1}$ | $ν_s$ $CH_2$ of lipids; Asymmetric $CH_2$ stretching mode of the methylene chains in membrane lipids |
| 2860 cm$^{-1}$ | Stretching C—H |
| 2874 cm$^{-1}$ | $ν_s$ $CH_3$; Stretching C—H, N—H; Symmetric stretching vibration of $CH_3$ of acyl chains (lipids) |
| 2884/85 cm$^{-1}$ | Stretching C—H |
| 2886/7/8/9/90 cm$^{-1}$ | Stretching C—H |
| 2893/4/6 cm$^{-1}$ | $CH_3$ symmetric stretch |
| 2916 cm$^{-1}$ | Cholesterol, phospholipids and creatine (higher in normal tissues); Stretching vibrations of $CH_2$ & $CH_3$ of phospholipids, cholesterol and creatine |

TABLE 1-continued

The spectral interpretations

Assignment

| Wavenumber | Assignment |
|---|---|
| 2917/8/9 cm$^{-1}$ | Stretching C—H |
| 2922 cm$^{-1}$ | Asymmetric stretching vibration of CH$_2$ of acyl chains (lipids) |
| 2923-33 cm$^{-1}$ | C—H stretching bands in malignant tissues |
| 2923/5 cm$^{-1}$ | Stretching C—H |
| 2925 cm$^{-1}$ | C—H stretching bands in normal tissues; $\nu_{as}$ CH$_2$ lipids |
| 2928 cm$^{-1}$ | Stretching C—H |
| 2930 cm$^{-1}$ | C—H stretching bands; $\nu_{as}$ CH2 |
| 2947/8 cm$^{-1}$ | Stretching C—H |
| 2951 cm$^{-1}$ | Stretching C—H |
| 2952 cm$^{-1}$ | CH$_3$ asymmetric stretch |
| 2951/3/5/6 cm$^{-1}$ | Stretching C—H |
| 2956 cm$^{-1}$ | Asymmetric stretching vibration of CH3 of acyl chains (lipids) |
| 2959 cm$^{-1}$ | C—H stretching; $\nu_{as}$ CH3 of lipids, DNA, and proteins; Asymmetric stretching mode of the methyl groups from cellular proteins, nucleic acids and lipids |
| 2960 cm$^{-1}$ | $\nu_{as}$ CH$_3$ |
| 2963 cm$^{-1}$ | CH$_3$ modes |
| 2965 cm$^{-1}$ | Stretching C—H |
| 2970 cm$^{-1}$ | $\nu_{as}$ CH$_3$, lipids, fatty acids |
| 2975 cm$^{-1}$ | Stretching N—H, stretching C—H |
| 2984 cm$^{-1}$ | CH$_{\alpha, \alpha'}$ stretch |
| 2993/4 cm$^{-1}$ | C—H ring |
| 2994 cm$^{-1}$ | CH$_{\alpha, \alpha'}$ stretch |
| 2998/9 cm$^{-1}$ | C—H ring |
| 3000 cm$^{-1}$ | C—H ring; CH stretching vibrations (remain unaltered by the methoxy and hydroxyl substitution) |
| 3000-600 cm$^{-1}$ | N—H stretching |
| 3000-700 cm$^{-1}$ | O—H stretching (water) |
| 3007 cm$^{-1}$ | C—H |
| 3007-10 cm$^{-1}$ | =C—H groups that are related to olefins bands or unsaturated fatty acids (absent in cancer samples) |
| 3008 cm$^{-1}$ | C—H ring; $\nu_{as}$ (=C—H), lipids, fatty acids |
| 3015 cm$^{-1}$ | $\nu$ =CH of lipids |
| 3015/17/20 cm$^{-1}$ | CH$_2$, aromatic stretch |
| 3021/2 cm$^{-1}$ | C—H ring |
| 3050 cm$^{-1}$ | Amid B (N—H stretching) |
| 3064 cm$^{-1}$ | C$_2$ aromatic stretching |
| 3070 cm$^{-1}$ | Fermi-enhanced overtone of the amide II band (at 1550 cm$^{-1}$) |
| 3072/4 cm$^{-1}$ | C—H ring |
| 3074 cm$^{-1}$ | CH stretching band of the phenyl rings; C$_2$—CH$_2$ aromatic stretching |
| 3075 cm$^{-1}$ | Amide B bands steming from N—H stretching modes in proteins and nucleic acids |
| 3078 cm$^{-1}$ | C—H ring |
| 3111/4/6 cm$^{-1}$ | C—H ring |
| 3163/82 cm$^{-1}$ | Stretching N—H symmetric |
| 3190 cm$^{-1}$ | N—H stretching bands of mainly cis-ordered substructures |
| 3194/5/7/9/200 cm$^{-1}$ | Stretching N—H symmetric |
| 3200-550 cm$^{-1}$ | Symmetric and asymmetric vibrations attributed to water. So it would be better not to consider this region for detailed analysis |
| 3201 cm$^{-1}$ | Stretching N—H symmetric |
| 3216/17/26 cm$^{-1}$ | Stretching O—H symmetric |
| 3273/87/89 cm$^{-1}$ | Stretching O—H symmetric |
| 3293 cm$^{-1}$ | OH stretching (associated) |
| 3295 cm$^{-1}$ | Amid A (N—H stretching) |
| 3300 cm$^{-1}$ | Amide A bands steming from N—H stretching modes in proteins and nucleic acids |
| 3301 cm$^{-1}$ | Amide A band |
| 3313 cm$^{-1}$ | Amide A band |
| 3320 cm$^{-1}$ | NH band |
| 3327 cm$^{-1}$ | Stretching N—H asymmetric |
| 3328 cm$^{-1}$ | Amide A band |
| 3330/5/7/9/43 cm$^{-1}$ | Stretching N—H asymmetric |
| 3350 cm$^{-1}$ | O—H, N—H, C—H |
| 3353 cm$^{-1}$ | Stretching N—H asymmetric |
| 3354 cm$^{-1}$ | O—H, N—H, C—H |
| 3359 cm$^{-1}$ | Stretching N—H asymmetric O—H, N—H, C—H |
| 3362 cm$^{-1}$ | O—H, N—H, C—H |
| 3396 cm$^{-1}$ | Stretching O—H asymmetric |
| 3401 cm$^{-1}$ | O—H & N—H stretching vibrations (hydrogen bonding network may vary in the malignant tissues) |
| 3410/16/20/22 cm$^{-1}$ | Stretching O—H asymmetric |
| 3430 cm$^{-1}$ | N—H stretching bands of mainly trans-ordered substructures |
| 3435/442 cm$^{-1}$ | Stretching O—H asymmetric |
| 3500-600 cm$^{-1}$ | OH bonds |
| 3506 cm$^{-1}$ | OH stretching (free) |

TABLE 1-continued

The spectral interpretations

| | Assignment |
|---|---|
| 3524/28/42 cm$^{-1}$ | Stretching O—H |
| 3561 cm$^{-1}$ | OH stretching (free) |
| 3570/77/78/82/90/9 cm$^{-1}$ | Stretching O—H |
| 3611 cm$^{-1}$ | O—H & N—H stretching vibrations (hydrogen bonding network may vary in the malignant tissues) |

The term "internal reflection element" or IRE refers to a crystal, prism, or other structure that will admit incoming radiation and reflect the radiation at least once from a surface on the interior of the element, preferably following interaction of the radiation with a sample in contact with the reflecting surface. Following such a reflectance, the radiation can be re-reflected or emitted from the element. Preferably the IRE comprises a germanium crystal, a zinc selenide crystal, or other material with higher index of refraction than the refractive index of the sample being read that are capable of transmitting IR or visible light.

The term "multi-pass ATR" refers to an attenuated total reflectance technique in which radiation that is incident on an internal reflectance element having two or more reflection faces within the IRE experiences two or more interactions with a reflection face before exiting the IRE. At these interfaces, the light is totally reflected back into the IRE material. Such interactions are typically referred to as "bounces" or "passes". Application of multi-pass ATR generates a multi-pass ATR spectrum. Typically, the IRE is in contact with a sample, the incident radiation is IR radiation and the exiting radiation subsequently interacts with a detector.

The term "single-pass ATR" refers to an attenuated total reflectance technique in which radiation incident on an internal reflectance element (IRE) having one or more reflection faces within the IRE experiences only one interaction with a reflection face before exiting the IRE. At this interface, the light is totally reflected back into the IRE material. Application of single-pass ATR generates a single-pass ATR spectrum.

The term "reflecting surface" refers to a surface capable of reflecting incident radiation. On the IR surface where the sample is deposited, the incident light is at an angle greater than the critical angle and hence experiences total internal reflection. There is no transmission of light at this interface, but rather an evanescent wave that escapes out of the surface of the IRE but is coupled back into the IRE material. Indeed, the technique of attenuated total internal reflection (ATR) is based on the principle that an evanescent wave interacts with a sample that is within one fifth of one wavelength of the dielectric boundary.

Attenuated total reflection (ATR) spectroscopy is predicated on the concept that, when light traveling within a medium impinges upon an interface between that medium and a medium of lower refractive index, it either passes into the second medium or is totally internally reflected, depending on whether the quantity $[n_1/n_2 \sin \theta_i]$ is less than or greater than one. In this relationship, $n_1$ and $n_2$ are the refractive indices of the first and second media, respectively, and $\theta_i$ is the angle of incidence. If $n_1/n_2 \sin \theta_i$ is greater than one, total internal reflection occurs. Although the internal reflection is referred to as total, the light, during the reflection process, penetrates a short distance into the second medium. The depth of penetration depends in a predictable fashion on the refractive indices of the two media and the angle of incidence, and is typically on the order of tenths of the wavelength of the light. If the incident light includes a wavelength absorbed by a constituent of the second medium, light of such wavelength will be partially absorbed or attenuated during reflection due to the penetration of the light into the second medium. This effect is referred to as attenuated total reflection. Due to the very shallow penetration of the light into the second medium, ATR is a useful technique for measuring absorbance by strongly absorbing materials. ATR has also been particularly useful for measuring absorbance of material deposited on a surface. Attenuated total reflection spectroscopy is widely used to collect an absorption spectrum from samples that are too opaque for direct absorption measurements.

In practice, one surface of an internal reflecting element (IRE) is placed in contact with a test sample. An incident beam of radiation is directed through the IRE so that it is totally internally reflected at the boundary between the IRE and the test sample. Some of the energy of the incident radiation is absorbed by the test sample through evanescent coupling. The amount of absorption is representative of the molecular structure and/or the molecular species found in the test sample. The reflected radiation, therefore, includes information from which an absorption spectrum for the test sample can be acquired. IREs utilizing total internal reflection or attenuated total reflection principles are commonly found in optical systems designed to analyze samples by assessing the optical constants of the sample and by establishing the physical and chemical composition thereof. Examples of IREs disposed in various optical systems are shown, for example, in U.S. Pat. Nos. 4,602,869 and 3,393,603. In some embodiments, the IRE is a germanium crystal or a zinc selenide crystal. The angle of incidence is defined as the angle between the ray direction and the normal to the surface. A 45-degree angle of incidence is often convenient for a multi-pass FTIR-ATR element. However, the angle of incidence and the composition of an element can be varied to optimize the parameters for a given experiment.

Mathematical and statistical operations that are performed in the course of practicing the present methods can be performed using any suitable computational equipment and software. For example, a commercially available personal computer can be used as a platform for software that can facilitate the acquisition of data, the calculation of difference spectra and perform spectral and other analysis. Computers networked with an FTIR instrument can be employed to acquire data on one machine and process it on another. Suitable data acquisition and management software packages can be designed and written de novo or can be purchased. Suitable commercially available software packages can include SCANTRAQ BASIC™ software package available from FTG Software Associates of Princeton, N.J., and GRAMS/32™ Version 5.2 software package, available from ThermoGalactic of Salem, N.H.

In some embodiments, the process of acquiring a spectrum of a sample is automated. Suitable commercially available software packages for automated spectrum acquisition include the WINFIRST™ package available from Thermo Mattson of Madison, Wis., and the AUTOPRO™ software package available from Pike Technologies, Inc. of Madison, Wis. These software packages can be employed to automate spectrum acquisition and can be useful for analyzing large numbers of samples. In some embodiments, the process is fully automated and can comprise an autosampler to inject and remove samples and a spectrum acquisition software package to run an FTIR microscope or FTIR bench accessory. Additionally, the identified software packages can be modified, or software can be written or purchased, to perform the various mathematical and statistical operations that can be performed when acquiring data by employing the present inventive methods. For example, software can be provided and employed to analyze an acquired spectrum, whereby the water component is automatically subtracted from the spectrum and the quality and quantity of secondary structure is subsequently identified using algorithms referred to, incorporated and disclosed herein. In this embodiment, a researcher can simply prepare the autosampler, configure the software and begin the process.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "cellular interaction" refers here to extracellular and intracellular interactions (e.g., between molecules on the surface of contacting cells, for example, receptor:ligand and m antibody:antigen interactions or internal molecules within signaling pathways associated with defenses). The molecules used to perturb cell biosensors can therefore be non-cell-associated molecules, such as extracellular antibodies and ligands that are interacting with other molecules on or within the cell, such as receptors or antigens. The molecules can also be endogenous molecules that are interacting on or within the cell as part of a signal cascade (e.g., triggered by an extracellular event).

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "environmental sample" refers to any sample taken from the environment for purposes of detecting cell activating agents in the sample. For example, the environmental sample can be a water sample, e.g., taken from an aquifer, stream, lake, or river. The environmental sample can also be a food sample. The environmental sample can also be from a solid surface, e.g., using a swab or other collection means.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Early Detection of CD3-Mediated T-Cell Activation by ATR-FTIR Spectroscopy The application of Infrared Spectroscopy to measure and identify cellular responses has numerous benefits (Erukhimovitch, V., et al., in DNA Viruses (Springer, 2005), pp. 161-172; Hastings, G., et al., Analyst (2009) 134(7):1462-1471; Lee-Montiel, F. T., et al., Journal of biological engineering (2011) 5:16). Cells in culture mount stimulus-specific responses that are induced by receptor:ligand interactions. As disclosed herein, one can use ATR-FTIR to identify specific cellular signals that define ligands, e.g., antibodies, pathogens, allergens, capable of interacting with cell surface receptors, thus exploiting the cell as a sensor. This provides a read-out that, in turn, can be used to identify specific cellular interactions. In its simplest form, direct observation of responses such as cytopathic changes induced by virus infections has been used historically to screen for viruses in cell culture. Confirmatory assays for specific pathogen identification depend on complex molecular methods and the use of biological and chemical probes depending on the signals to be detected. These assays are generally elaborate, and require specific reagents and complex methods usually requiring a range of three hours (Erukhimovitch, V., et al., Analyst (2011) 136(13):2818-2824) to weeks where there is sufficient material for detection, or up to months when there is not. Measurement of cellular responses to stimuli is also very useful for the identification of normal immune responses or, alternatively, disease or infection states. Cellular responses engage immediately after a cell detects a foreign agent, a stimulant, an antibody, or a pathogen. ATR-FTIR, which greatly reduces background noise, is more sensitive to the events occurring on the cell membrane compared to transmission FTIR since the interrogating light penetrates only about 2 microns into the cell suspension rather than the entire thickness of the cell suspension spot as in transmission FTIR. The ATR-FTIR configuration also produces better resolution of spectral features. This is confirmed by the features seen in FIG. 1 Inset b, where more details with better signal-to-noise ratio are visible in the ATR-FTIR absorbance curve compared to the FTIR absorbance curve. The use of Fourier Transform Infrared Spectroscopy (FTIR) is reported, employing the Attenuated Total Reflectance (ATR) technique to detect early activation events in Jurkat T-cells after the binding of their cell surface CD3-receptors by a specific antibody (anti-CD3) at 75 minutes post stimulation. One can identify, using this rapid and non-intrusive method, the spectral patterns of cells undergoing activation events and show them to be distinct from their control counterparts under the same conditions. This method will also allow the interrogation of the cells at time points as early as five minutes post stimulation.

ATR-FTIR Spectroscopy

When electromagnetic radiation passes through a material, photons with certain frequencies of light are absorbed while the rest are transmitted. These absorbed frequencies of light correspond to the vibrational frequencies of atomic and molecular bonds. Thus FTIR spectroscopy is able to identify the chemical composition of specific materials. FTIR spectroscopy is employed to detect changes in materials that are exposed to specific reagents. ATR is a particular configuration where light is totally internally reflected inside a prism of high refractive index (FIG. 1 Inset a). The prism material used in the following experiments was Zinc Selenide (ZnSe) crystal. Some photons penetrate out of the surface of the crystal, and then are coupled back in. This evanescent wave can interact with any material on the surface of the crystal and thus the intensities of the frequencies of light measured after passing through the prism are highly sensitive to the materials present on the surface of the crystal. Five microliter aliquots of cell suspension (~625,000 cells) were spotted on ZnSe ATR crystal and allowed to air dry. The samples were scanned in the mid-infrared range (1500 to 800 $cm^{-1}$). The ATR configuration allowed for light to penetrate an average depth of 2 microns into the cell suspension at the given frequency range. The penetration depth, however, is a function of the incident wavelength.

The ATR absorption spectra initially revealing the peaks characteristic of the interrogated medium are shown in FIG. 1. As the water evaporated (~15 minutes), the cells settled to the surface of the crystal and peaks representative of the biological material composition of the cells such as proteins, DNA, and phospholipids in addition to that of the medium were captured.

Sample Preparation

Jurkat T-cells were chosen as model biosensors to be interrogated using the ATR-FTIR spectroscopic technique. The Clone E6-1 cells (ATCC #TIB-152) were grown in log-phase in R-10 growth medium (RPMI-1640, (Mediatech Manassas, Va.); supplemented with 10% FBS, 100 U/ml penicillin, and 100 μg/ml streptomycin). Cells were counted and checked for viability by the trypan blue exclusion method and only cells with >95% viability was accepted as sensors. The cells were then aliquoted into about a million cells each in sterile capped 1.5 ml vials, and centrifuged at room temperature for four minutes at 800 g. The growth medium was then completely removed and replaced with 100 μl of either fresh R-10, a matched isotype control antibody, or with R-10 supplemented with 100 ng/ml anti-CD3 antibody (Mabtech, Nacka Strand, Sweden). The cells were gently mixed and incubated in a humidified chamber at 37° C. in 5% $CO_2$ for 75 minutes with the vial lids loosened to allow for gas exchange. At the end of the incubation, the contents of two vials with the same treatment conditions were then pooled together (two million cells per vial). Ice-cold unsupplemented RPMI-1640 medium (1 ml) was added to each vial, which was then centrifuged at 800 g for four minutes at room temperature. The supernatant was removed and the pellet washed a second time with one ml of ice-cold unsupplemented RPMI-1640 medium after which the supernatant was removed completely. The pellet of two million cells was re-suspended in 16 μl of cold, fresh, unsupplemented RPMI-1640 medium, placed on ice and transported to the neighboring FTIR facility to be read using the Bruker Vertex 70 FTIR spectrometer. Jurkat cells without the anti-CD3 antibody treatment or with an equivalent amount of isotype antibody were used as negative controls. A five microliter drop (~625,000 cells) was spotted onto the ZnSe crystal and allowed to air dry.

Post Processing of Data

Spectral data were collected in the range of 1500 to 800 $cm^{-1}$ for the activated and unactivated (control) cells. Some moisture absorption lines from the background were corrected. In later experiments, the water noise was further reduced by employing an ATR with dry air purging capability. A five point moving average was performed and the spectrum was vector normalized where the average of all the absorbance values of the spectrum was subtracted from the entire spectrum. This reduced the mid-spectrum to zero. Then the sum of the squares of all the absorbance values was calculated and the spectrum divided by the square root of this sum.

Analysis and Results

Figure 2:
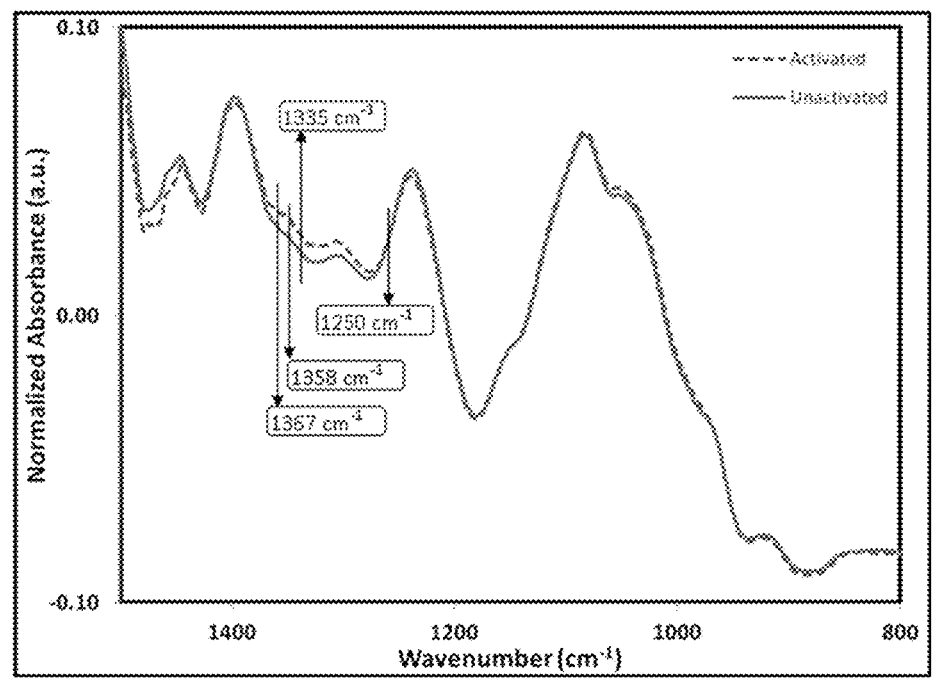
FIG. 2 is an ATR spectrum of cells treated with an activating antibody and cells treated with a control IgG isotype, indicating spectral markers whose absorbance values differentiate the activated from the unactivated cells. The markers are: 1367 $cm^{-1}$, 1358 $cm^{-1}$ (Deformation of C—H and N—H), 1335 $cm^{-1}$ (C—H stretching) and 1250 $cm^{-1}$ (Amide III of proteins).

The vector normalized ATR spectra reveal some marked differences between the activated and unactivated cell sensors (FIG. 2). The activated state of the experimentally treated cells and the unactivated state of the control cells have been validated by data from parallel flow cytometry experiments monitoring the cells for 24 hours post treatment for the presence of cell surface expression of the activation marker CD69 as measured by a BD LSRFortessa (BD BioSciences, San Jose, Calif.). Five repeat spectra for each set were collected and each spectrum was an average of 50 separate scans. Specific frequencies at which the absorbance varied between the activated and the unactivated cells were identified. Four spectral frequencies namely, 1358, 1367, 1335 and 1250 $cm^{-1}$ were selected and the differences between the absorbances at these identified frequencies were considered as the differentiating markers. A two-tailed paired student's t-test was performed by using the absorbance values at the chosen markers and was followed by post-hoc Bonferroni corrections for multiple comparisons with false discovery rate analysis. A confidence interval of 95% was chosen as a test of significance. Of the four spectral markers (Table 2), the differences at 1358 $cm^{-1}$ and 1367 $cm^{-1}$ efficiently distinguished the activated from the unactivated cells at 75 minutes after cell incubation with anti-CD3 antibody in eleven independent experiments with p-values of 0.02. The markers at 1335 $cm^{-1}$ and 1250 $cm^{-1}$ have p values of 0.028 and 0.038 respectively.

TABLE 2

Paired t-tests on selected spectral bands, corrected for multiple comparisons with false discovery rate analysis.

| Comparisons | Wavenumber ($cm^{-1}$) | Paired t-test Significance | Post-hoc Bonferroni Correction | Statistically Significant? |
|---|---|---|---|---|
| 1 | 1358 | 0.020 | 0.050 | Yes |
| 2 | 1367 | 0.020 | 0.025 | Yes |
| 3 | 1335 | 0.028 | 0.017 | No |
| 4 | 1250 | 0.038 | 0.013 | No |

Discussion and Conclusion

ATR-FTIR spectroscopic tool has been successfully used for the first time to rapidly detect Jurkat cells early activation events mediated by exposure of cells to antibody specific to the CD3 T cell co-receptor. Cells were interrogated 75 minutes post exposure and the ratios of specific absorbance values of the cells were calculated and used to differentiate treatment groups. These experiments have validated that the treatment conditions mediate T-cell activation determined by CD69 cell surface expression. Ligation of the T-cell receptor, which occurs by treatment of the cells with anti-CD3, activates T cells by modulating specific molecular events including the assembly of specific activation complexes that initiate after the recruitment of ZAP-70 to the cytoplasmic domain of ligated CD3. Ultimately, correlation of the spectral changes with activation of signaling events induced by specific agents may enhance understanding of the relationship between spectral changes and recruitment of specific molecular interactions.

Figure 4:
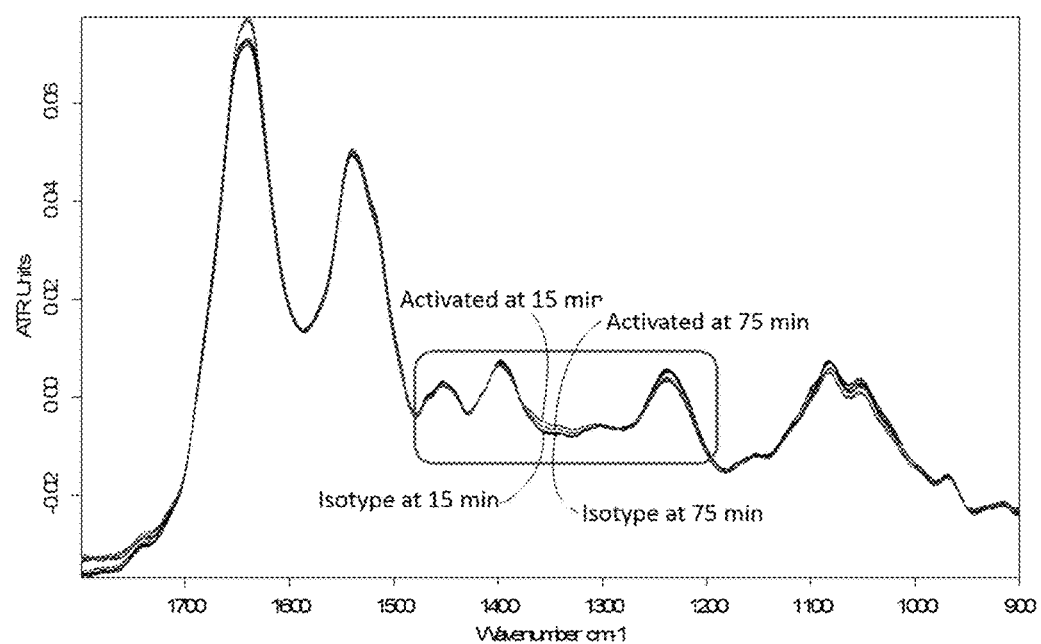
FIG. 4 is an ATR spectra showing a difference at 1200-1500 $cm^{-1}$ range between activated and unactivated samples at 15 and 75 min time points.

Example 2: Detection of Cell Activation by ATR-FTIR Spectroscopy at 15 Minutes Post Exposure Jurkat T-cells were exposed to both anti-CD3 and anti-CD28 which is a well-accepted method of activating Jurkat cells to proliferate and produce specific cytokines. The activated T-cells were interrogated by ATR-FTIR at 15 min and 75 min post exposure to the activating agent. The control sample for the experiment was T-cells exposed to a non-specific IgG isotype of the antibodies used. ATR-FTIR spectra showed marked differences in the 1200-1500 $cm^{-1}$ region between activated and unactivated t-cell samples at 15 and 75 min post exposure (FIG. 4). The isotype control was ratified by plotting 5 reads of the isotype at 15 and 75 min with nearly identical spectra. Detection of activation at 15 min post exposure has been successfully observed in three independent experiments. More repeats are underway on which statistical analysis will be performed.

Figure 3:
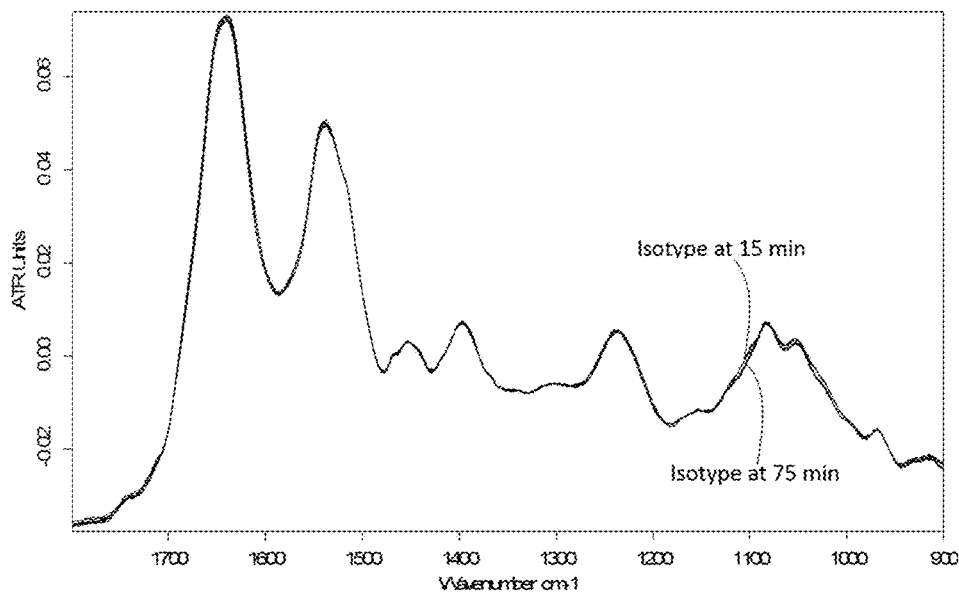
FIG. 3 is an ATR spectra of IgG isotypes (impotent activating agents that have the same m chemical composition as that of the activating agents) read at 15 and 75 min. Note that there are 5 reads plotted for each sample to show the reproducibility.

FIG. 3 is an ATR spectra of isotypes (impotent activating agents that have the same chemical composition as that of the activating agents) read at 15 and 75 min. Note that there are 5 reads plotted for each sample to show the reproducibility.

FIG. 4 is an ATR spectra showing a difference at 1200-1500 $cm^{-1}$ range between activated and unactivated samples at 15 and 75 min time points.

Figure 5:
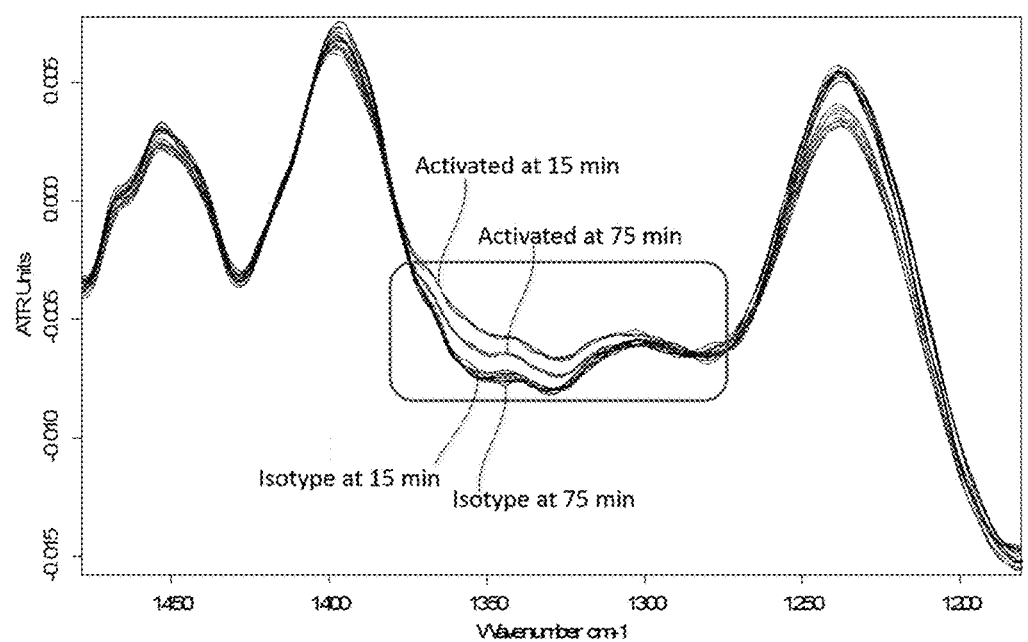
FIG. 5 is an ATR spectra showing a difference at 1300-1375 $cm^{-1}$ range between activated and unactivated samples at 15 and 75 min.

FIG. 5 is an ATR spectra showing a difference at 1300-1375 $cm^{-1}$ range between activated and unactivated samples at 15 and 75 min.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for detecting a cellular response resulting from a defined treatment or exposure, comprising
   (a) depositing a sample comprising a plurality of cells under reaction conditions on an internal reflection element (IRE);
   (b) directing a beam of infrared (IR) radiation through the IRE under conditions such that the IR radiation interacts with the plurality of cells;
   (c) recording an absorption spectrum over a range of preselected frequencies; and
   (d) comparing the absorption spectrum to a control spectrum;
   wherein a change in absorbance at one or more frequencies compared to the control spectrum is an indication of a cellular interaction in the plurality of cells; and
   wherein the reaction conditions comprise contacting the plurality of cells with a sample comprising one or more potential pathogens, allergens, or ligands.

2. The method of claim 1, wherein the potential pathogen is a virus, bacteria, or yeast.

3. The method of claim 1, wherein the potential ligand is selected from the group consisting of antibodies, growth factors, cytokines, chemokines, hormones, extracellular matrix proteins, and cell-surface proteins.

4. The method of claim 1, wherein the potential ligand is selected from the group consisting of proteins, peptides, peptide nucleic acids, and small molecules.

5. The method of claim 1, wherein the reaction conditions further comprise a change in temperature, pH, salinity, or any combination thereof.

6. The method of claim 1, wherein the cellular interaction is detected within 15 minutes to 75 minutes.

7. The method of claim 1, wherein the plurality of cells comprise bacterial or yeast cells.

8. The method of claim 1, wherein the plurality of cells comprise mammalian cells.

9. The method of claim 1, wherein the plurality of cells comprise a transformed cell line.

10. The method of claim 1, wherein the range of preselected frequencies is between 50 $cm^{-1}$ and 3700 $cm^{-1}$.

11. The method of claim 10, wherein the range of preselected frequencies is between 800 $cm^{-1}$ and 1500 $cm^{-1}$.

12. The method of claim 1, wherein the IRE is an attenuated total reflectance (ATR) crystal comprising an optical material with a higher refractive index than the sample comprising the plurality of cells.

13. The method of claim 12, wherein the IRE comprises a germanium crystal or a zinc selenide crystal.

14. The method of claim 1, wherein the IR radiation that interacts with the plurality of cells is an evanescent wave with an average penetration depth of about 2 μm.

15. The method of claim 1, further comprising Fourier transformation of the absorbance spectrum.

16. A method for using cells as a biosensor, comprising:
   (a) exposing a homogeneous population of cells with a sample;
   (b) depositing the homogeneous population of cells on an internal reflection element (IRE);
   (c) directing a beam of infrared (IR) radiation through the IRE under conditions such that the IR radiation interacts with the plurality of cells;
   (d) recording an absorption spectrum over a range of preselected frequencies; and
   (e) comparing the absorption spectrum to a control spectrum;
   wherein a change in absorbance at one or more frequencies compared to the control spectrum is an indication of a cell activating agent in the sample; and
   wherein the cell activating agent comprises one or more potential pathogens, allergens, or ligands.

17. A system for detecting a cell activating agent in a sample, comprising:
   (a) a Fourier transform infrared spectrometer configured with an internal reflection element (IRE) for attenuated total reflectance (ATR); and
   (b) a homogeneous population of cells selected to react with the cell activating agent; and
   wherein the cell activating agent comprises one or more potential pathogens, allergens, or ligands.

* * * * *